United States Patent
Beyer et al.

(10) Patent No.: US 11,603,354 B2
(45) Date of Patent: Mar. 14, 2023

(54) INTERMEDIATE COMPOUNDS AND METHODS

(71) Applicant: Boehringer Ingelheim International GmbH, Ingelheim am Rhein (DE)

(72) Inventors: Phouvieng Beyer, New Milford, CT (US); Jason A. Brazzillo, Cortlandt Manor, NY (US); Weitong Dong, Sandy Hook, CT (US); Magnus Eriksson, Brookfield, CT (US); Jon Charles Lorenz, New Milford, CT (US); Laurence J. Nummy, Newburgh, NY (US); Sonia Rodriguez, Avon, CT (US); Jolaine Savoie, Sandy Hook, CT (US); Kanwar Pal Singh Sidhu, Orange, CT (US); Joshua D. Sieber, Richmond, VA (US); Thomas Gabriel Tampone, Southbury, CT (US); Zhulin Tan, Cheshire, CT (US); Jun Wang, New Milford, CT (US); Li Zhang, New Milford, CT (US); Pengtao Zhang, Shanghai (CN)

(*) Notice: Subject to any disclaimer, the term of this patent is extended or adjusted under 35 U.S.C. 154(b) by 0 days.

(21) Appl. No.: 17/375,322

(22) Filed: Jul. 14, 2021

(65) Prior Publication Data
US 2021/0340101 A1    Nov. 4, 2021

Related U.S. Application Data

(63) Continuation of application No. 16/635,182, filed as application No. PCT/US2018/044279 on Jul. 30, 2018, now abandoned.

(60) Provisional application No. 62/539,762, filed on Aug. 1, 2017.

(51) Int. Cl.
C07D 209/54    (2006.01)

(52) U.S. Cl.
CPC ................... C07D 209/54 (2013.01)

(58) Field of Classification Search
CPC .................................................. C07D 209/54
See application file for complete search history.

(56) References Cited

U.S. PATENT DOCUMENTS

| | | |
|---|---|---|
| 8,940,893 B2 | 1/2015 | Bosanac et al. |
| 9,156,847 B2 | 10/2015 | Pye et al. |
| 10,138,229 B2 | 11/2018 | Bentzien et al. |
| 10,875,852 B2 | 12/2020 | Bentzien et al. |
| 2006/0019985 A1 | 1/2006 | Ma et al. |
| 2014/0275014 A1 | 9/2014 | Bosanac et al. |
| 2016/0159774 A1 | 6/2016 | Schwartz et al. |
| 2016/0340339 A1 | 11/2016 | Bentzien et al. |
| 2018/0009814 A1 | 1/2018 | Benhaim et al. |

FOREIGN PATENT DOCUMENTS

| | | |
|---|---|---|
| CN | 1665818 A | 9/2005 |
| CN | 102382129 A | 3/2012 |
| CN | 104080789 A | 10/2014 |
| CN | 104603124 A | 5/2015 |
| JP | 2015524480 A | 8/2015 |
| JP | 2016510779 A | 4/2016 |
| JP | 2016513675 A | 5/2016 |
| JP | 2017504634 A | 2/2017 |
| WO | 2004005293 A2 | 1/2004 |
| WO | 2006012443 A1 | 2/2006 |
| WO | 2013113097 A1 | 8/2013 |
| WO | 2014025976 A1 | 2/2014 |
| WO | 2014139970 A1 | 9/2014 |
| WO | 2014152114 A1 | 9/2014 |
| WO | 2015116485 A1 | 8/2015 |
| WO | 2016115356 A1 | 7/2016 |

OTHER PUBLICATIONS

International Search Report PCT/US2018/044279 filed Jul. 30, 2018.
Huang, Jamin et al., "Synthesis of 1,3,4-Oxadiazol-2-ones with Aliphatic Groups at N-3," Journal of Heterocyclic Chemistry, 1987, vol. 24, pp. 1-7.
Magnus, Philip et al., "Lewis Acid Catalyzed a-Functionalization of Ketals for the Regioselective Synthesis of a-Carbamoyl Ketals," Organic Letters, 2012, vol. 14, No. 15, pp. 3952-3954.
Kulkarni et al. "1, 3?disubstituted?4?aminopyrazolo [3,4?d] pyrimidines, a new class of potent inhibitors for Phospholipase D." Chemical Biology & Drug Design. vol. 84.3. 2014. pp. 270-281.
Aggarwal et al. "Synthesis and NMR spectral studies of some new 1-heteroaryl-5-amino-3-alkyl/aryl-4-cyanopyrazoles." Indian Journal of Chemistry. vol. 45B. 2006. pp. 1426-1430.
Liu, et al. "Base-catalyzed one-pot tandem reaction: an effective strategy for the synthesis of pyrazolo [3,4-d] pyrimidinone derivatives." Tetrahedron. vol. 71.40. 2015. pp. 7658-7662.
Toshihiko Kaneko, et al.: "Piperidine carboxylic acid derivatives of 10H-pyrazino[2,3b] [1,4]benzothiazine as orally-active adhesion molecule inhibitors", Chemical & Pharmaceutical Bulletin.

*Primary Examiner* — Shawquia Jackson
(74) *Attorney, Agent, or Firm* — John Esteban Ezcurra

(57) ABSTRACT

The present invention relates to compounds of (II) and an acceptable salt or hydrate thereof method of making same.

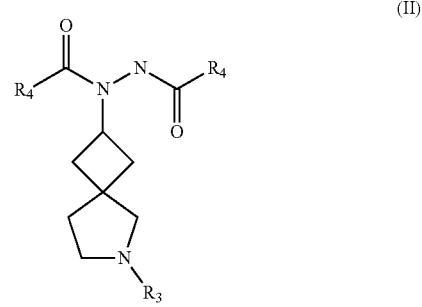

2 Claims, No Drawings

INTERMEDIATE COMPOUNDS AND METHODS

FIELD OF THE INVENTION

This invention relates to novel intermediates and methods of making them.

BACKGROUND OF THE INVENTION

Substituted hydrazine intermediates, with the general structure shown below, are versatile intermediates and nucleophiles useful for making heterocyclic compounds such as pyrazoles, and pyridazines as well as pesticides and pharmaceuticals (see, e.g. Kulkarni et al. Chem Biol. Drug Des 2014 (84), 270-281, Aggarwal et al. Indian J. Chem. 2006, 45B, 1426-1430, Liu et al. Tetrahedron 2015, 7658-7662).

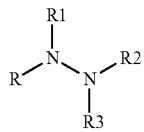

In particular, hydrazines substituted with alkyl, cycloalkyl and spirocyclic rings have found recent use in novel pharmaceutical applications directed towards treatment of immunology and oncology disorders (e.g. WO 2016115356, U.S. Pat. No. 9,156,847 B2). Consequently, there remains a need for additional derivatives of hydrazine that may be useful in the synthesis of pharmacologically relevant compounds.

SUMMARY OF THE INVENTION

The invention relates to novel intermediate compounds and methods for their preparation.

In a first aspect, the present invention relates to an intermediate compound of formula (II):

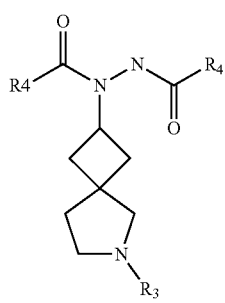

(II)

wherein R3 is chosen from hydrogen, halogen, halo C1-4 alkyl, C1-4 alkyl, C1-4 alkoxy, —CN, halo C1-4 alkoxy, acyl, acyloxy, alkylaryl or cycloalkyl; and R4 is hydrogen, halogen, halo C1-4 alkyl, C1-4 alkyl, C1-4 alkoxy, aryloxy, cycloalkyl, alkylaryl; or an acceptable salt or hydrate thereof.

In a second aspect, the present invention relates to a process for preparing the compound of formula (II) comprising the steps of:

(i) Converting a ompound of formula F to a compound of formula F1

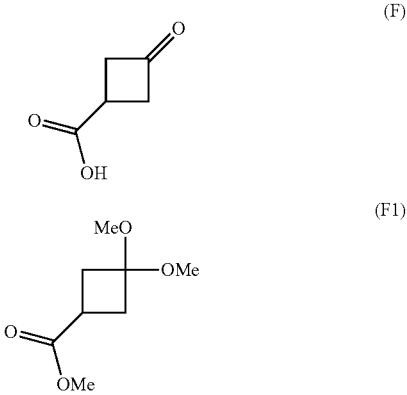

(ii) Coupling of a compound of formula F1 with compound F2 and conversion through additional steps to a compound of formula F3

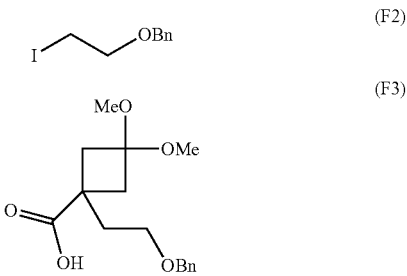

(iii) Conversion of compound F3 through additional steps to a compound of formula F4

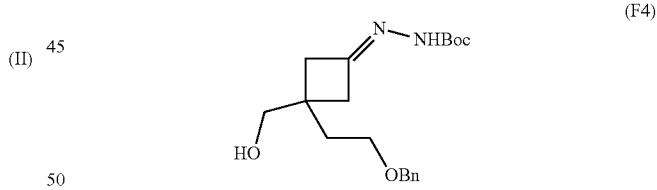

(iv) Conversion of compound F4 to a compound of formula F5

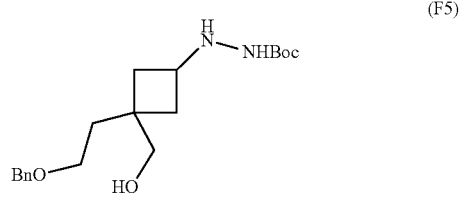 [SMILES: CC(C)(C)OC(=O)NNC1CC(CO)(CCOCc2ccccc2)C1]

(v) Conversion of compound F5 through additional steps to a compound of formula F6

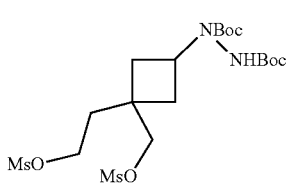

(F6)

(vi) Conversion of compound F6 to a compound of formula II

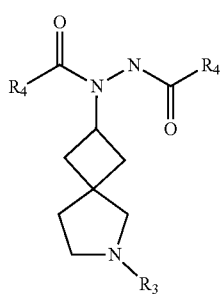

(II)

wherein R3 is chosen from hydrogen, halogen, halo C1-4 alkyl, C1-4 alkyl, C1-4 alkoxy, —CN, halo C1-4 alkoxy, acyl, acyloxy, alkylaryl or cycloalkyl; and R4 is hydrogen, halogen, halo C1-4 alkyl, C1-4 alkyl, C1-4 alkoxy, aryloxy, cycloalkyl, alkylaryl; or an acceptable salt or hydrate thereof.

DETAILED DESCRIPTION OF THE INVENTION

Substituted hydrazine intermediates are versatile intermediates and nucleophiles useful for making heterocyclic compounds such as pyrazoles, and pyridazines as well as pesticides and pharmaceuticals However, the inventors are not aware of any publications that teach the compounds of the present invention and their use for large-scale commercial production of pyrazoles or pyridazines.

All terms as used herein in this specification, unless otherwise stated, shall be understood in their ordinary meaning as known in the art. Other more specific definitions are as follows:
$K_2CO_3$=potassium carbonate
MeCN=acetonitrile
NaOH=sodium hydroxide
$iPr_2EtN$=ethyl diisopropylamine
$POC_{13}$=phosphorous oxychloride
NaOMe=sodium methoxide
MeOH=methanol
NHBoc=tert-butoxycarbonyl protecting group
BocN=tert-butoxycarbonyl protecting group
BuOH=1-butanol
Ms=methanesulfonyl; mesylate
IBCF=isobutyl chloroformate
NMM=4-methylmorpholine (N-methyl morpholine)
EtOH=ethanol
Protecting group=tert-butoxycarbonyl (Boc), phenoxycarbonyl (Cbz)

The term "$(C_1-C_4)$alkyl" refers to branched and unbranched alkyl groups having from 1 to 4 carbon atoms. Examples of —$(C_1-C_4)$alkyls include methyl, ethyl, n-propyl, isopropyl, n-butyl. It will be understood that any chemically feasible carbon atom of the $(C_1-C_4)$alkyl group can be the point of attachment to another group or moiety.

The term "halo" or "halogen" refers to fluoro, chloro, bromo or iodo.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

Certain compounds used in the processes of the invention may exist as salts formed from inorganic and organic acids. Such acids may be employed in preparing and/or isolating certain intermediates. For convenience, such acids are referred to herein as "salt-forming acids" and the salts formed from such salt-forming acids are referred to herein as "salt adducts." A nonlimiting example of a useful salt-forming acid is oxalic acid.

As noted above, the invention relates in one embodiment to methods of making the compounds of formula (II). Methods of making the compounds of formula (II) according to the invention are described below where the R groups are as defined above.

A nonlimiting method for making the compound of formula (II) according to the invention is depicted in Scheme 2 below.

Scheme 2

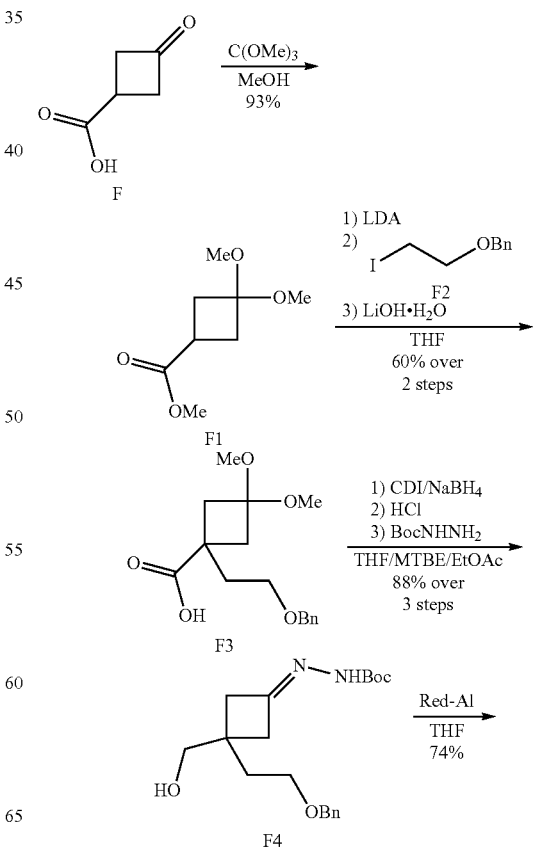

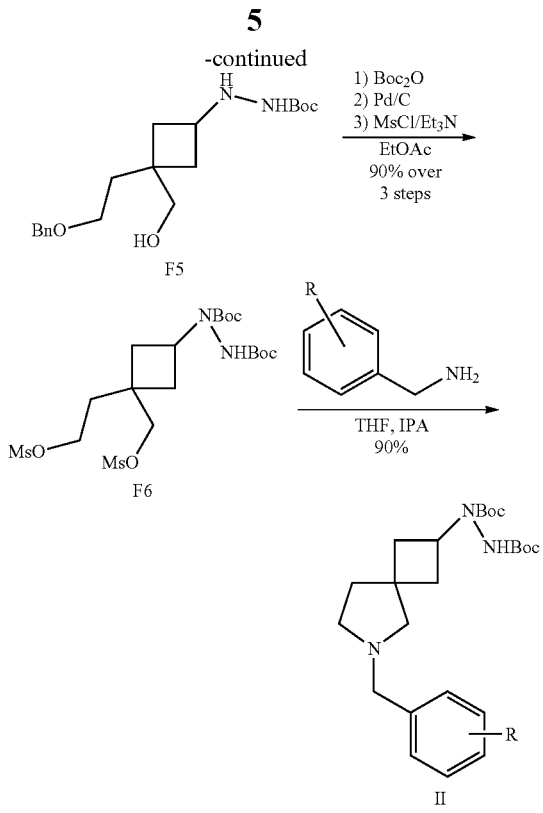

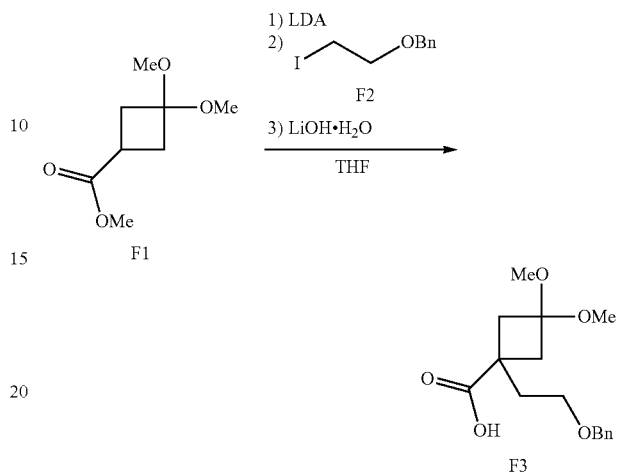

1.1.1. General Procedure for the Synthesis of Compounds of Formula F1

To a 1 L Chemglass reactor equipped with mechanical stirrer, reflux condenser, argon inlet and thermocouple with $T_{jacket}=22°$ C. was added compound F (1.0 equiv.), p-toluenesulfonic acid monohydrate (0.03 equiv.), Methanol HPLC Plus 99.9% (5 volumes) and Trimethylorthoformate (1.25 volumes). The resulting solution was heated at reflux ($T_{batch}=52$-$53°$ C.) with $T_{jacket}=65°$ C. for 1-2 hours. A sample after 1 h reflux analyzed by $^1$H-NMR (0.075 mL rxn sample diluted with 1.5 mL d$^6$-DMSO) showed complete conversion. Distilled trimethyl orthoformate and methanol at 50° C./<200 torr until no more solvent came off. Diluted with methyl tert-butyl ether (5 volumes) and washed organic layer with 5% $Na_2CO_3$ (2.5 volumes) twice and once with aq. 3% NaCl (2.5 volumes). The organic layer was concentrated at 50° C./<200 torr to give compound F1 as a yellow oil in 90-95% yield.

methyl 3,3-dimethoxycyclobutane-1-carboxylate

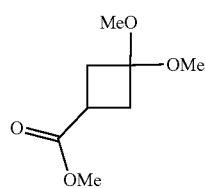 [SMILES: COC(=O)C1CC(OC)(OC)C1]

$^1$H-NMR (DMSO-d$^6$); δ3.61 (s, 3H), 3.06 (s, 3H), 3.03 (s, 3H), 2.80-2.90 (m, 1H), 2.33-2.42 (m, 2H), 2.17-2.25 (m, 2H). $^{13}$C-NMR (DMSO-d$^6$); 174.6, 99.3, 51.6, 48.1, 47.7, 34.9, 27.8.

1.2.1. General Procedure for the Synthesis of Compounds of Formula F3

To a 1 L reactor equipped with mechanical stirrer, thermocouple, reflux condenser and argon inlet was added diisopropylamine (1.1 equiv.) and anhydrous tetrahydrofuran (5 volumes based on compound F1). The solution was stirred under argon and cooled to <−20° C. with $T_{jacket}=-30°$ C. BuLi 2.5M hexanes (1.1 equiv.) was added slowly, keeping $T_{batch}<-10°$ C. The light yellow solution of LDA was stirred for 10 min and then compound F1 (1.0 equiv.) was added dropwise over 45-50 minutes, keeping $T_{batch}<-20°$ C. The resulting orange solution was stirred at $T_{jacket}=-30°$ C. for ca. 10 minutes. The [(2-iodoethoxy)methyl]benzene (F2) (1.0 equiv.) was added dropwise over ca. 10 minutes, leading to a reddish orange solution. The addition was slightly exothermic and the internal temperature rose to ca. −17° C. by the end of the addition. Set $T_{jacket}=-20°$ C. and stirred. The exotherm continued for about 10 minutes to ca. −6.4° C. when the internal temperature started to decrease. A yellow suspension formed within ~60 minutes stirring at $T_{jacket}=-20°$ C. The reaction was quenched with half-saturated NH$_4$Cl (5 volumes) after 2 hours stirring. Warmed reaction to room temperature and separated layers. Washed organic layer with water (3.5 volumes) and concentrated under reduced pressure at 40° C./100 mbar to a yellow oil. The oil was diluted with methanol (2.5 volumes based on compound F1) and tetrahydrofuran (2.5 volumes based on compound F1). The solution was stirred under argon and a solution of lithium hydroxide hydrate (1.0 equiv. based on Compound F1) in water (3 volumes based on Compound F1) was added in one portion. The mixture was stirred at $T_{jacket}=75°$ C. for 2-3 hours after which HPLC analysis indicated complete hydrolysis of the ester. The batch was cooled and concentrated under reduced pressure at 40° C./100 mbar to remove MeOH and THF and reduce volume to about 40% of original. The residual oil was diluted with methyl tert-butyl ether (2 volumes based on compound F1) and filtered through a pad of Celite. The filter pad was rinsed with methyl tert-butyl ether followed by water (2 volumes based on compound F1). The mixture was allowed to settle and the top organic layer was discarded. The aqueous layer was washed with methyl tert-butyl ether (2 volumes based on compound F1) and the top organic layer was discarded. Charged n-heptane (3.5 volumes based on compound F1) and stirred the mixture. Added 2M aq. hydrochloric acid (~0.4 equiv.) to reactor, and then added seeds. The temperature was set to $T_{jacket}$=5-7° C. and 2M aq. hydrochloric acid (~0.3 equiv.) was charged slowly over ca 20 minutes, keeping batch temperature <20° C., until pH was ~4. The suspension was cooled to ~10° C. and stirred for about 30 minutes. The slurry was filtered on a medium Buchner frit and the cake washed with n-Heptane (0.5 volumes) followed by water (1.0 volumes). The cake was dried on the frit with house-vacuum to afford 60-62% yield of compound F3 as off-white sugar-like crystals.

1-(2-(benzyloxy)ethyl)-3,3-dimethoxycyclobutane-1-carboxylic acid

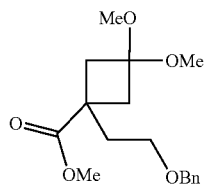 [SMILES: COC(=O)C1(CCOCc2ccccc2)CC(OC)(OC)C1]

$^1$H-NMR (DMSO-d$^6$); δ12.3 (br s, 1H), 7.23-7.37 (m, 5H), 4.41 (s, 2H), 3.39 (t, J=6.7 Hz, 2H), 3.03 (s, 3H), 3.00 (s, 3H), 2.44 (d, J=13 Hz, 2H), 2.08 (d, J=13 Hz, 2H), 2.01 (t, J=6.7 Hz, 2H). $^{13}$C-NMR (DMSO-d$^6$); 177.0, 138.5, 128.2, 127.3, 98.5, 72.0, 66.7, 47.8, 47.7, 40.1, 37.3, 36.4.

1.3.1. General Procedure for the Synthesis of Compounds of Formula F4

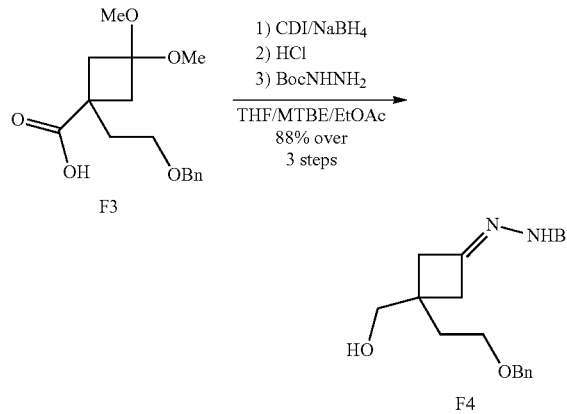

To a 1 L reactor equipped with mechanical stirrer, thermocouple, reflux condenser and argon inlet was added CDI (66.11 g, 407.7 mmol mmol) and THF (200 mL). A solution of compound F3 (100 g, 339.7 mmol) in THF (300 mL) was added over about 20 min. The resulting solution was stirred at room temperature for about 30 min. To another reactor, sodium borohydride (12.85 g, 339.7 mmol) was charged followed by cold (~5° C.) water (400 mL). The solution was cooled to 2~3° C. The THF solution was then charged over 15~30 min, keeping internal temperature below 35° C. and the resulting mixture was stirred for about 20 min at 20~35° C. The reaction mixture was concentrated by vacuum distillation, keeping internal temperature below 45° C., to half of its original volume. MTBE (400 mL) was charged and the mixture filtered to remove the solids. The cake was rinsed with MTBE (50 mL) and water (50 mL). The combined filtrates were stirred for about 10 minutes and the layers separated. The bottom aqueous layer was drained. Aqueous 1M HCl (300 mL) was added to the organic layer, the mixture stirred for 10 min the layers separated. The bottom aqueous layer was drained. Aqueous 1M HCl (300 mL) was added and the mixture stirred for 2 h at 18~22° C. The layers were separated and the bottom aqueous layer was drained. The organic layer was washed with aqueous 5% Na$_2$CO$_3$ (200 mL) followed by 3% NaCl (200 mL). The reaction mixture was concentrated by vacuum distillation, keeping internal temperature below 40° C., until about 15% of original volume remained to half of its original volume. Ethyl acetate (300 mL) was charged and distillation continued until about 25% of original volume remained. Ethyl acetate (300 mL) was charged and water content determined using Karl-Fischer to make sure the amount was <0.1%. Repeat distillation as necessary. To another reactor, Boc-hydrazine H$_2$NNHBoc (49.39 g, 373.7 mmol) and heptane (900 mL) were charged and stirred. The ethyl acetate solution was charged followed by acetic acid (10.20 g, 169.9 mmol) and seed crystals of compound F4 (0.002 g). The resulting suspension was stirred for about 30 min. The mixture was cooled to ~5° C. and stirred for 30 min. The slurry was filtered and the cake washed with 5:1 heptane/EtOAc (180 mL) and dried for 2 hours then in a vacuum oven at <40° C. to afford 85-90% yield of compound F4.

tert-butyl-2-(3-(2-(benzyloxy)ethyl)-3-(hydroxymethyl)cyclobutylidene)hydrazine-1-carboxylate $^1$H-NMR (CDCl$_3$); δ7.48 (br s, 1H), 7.27-7.37 (m, 5H), 4.50 (s, 2H), 3.40-3.62 (m, 5H), 2.75 (d, J=16 Hz, 1H), 2.60-2.68 (m, 2H), 2.45 (d, J=16 Hz, 1H), 1.92 (t, J=5.3 Hz, 2H), 1.50 (s, 9H). $^{13}$C-NMR (CDCl$_3$); 150.7, 137.4, 128.6, 128.0, 127.8, 81.6, 73.4, 68.1, 67.1, 41.9, 39.2, 37.1, 37.0, 28.3.

1.4. General Procedure for the Synthesis of Compounds of Formula F5

-continued

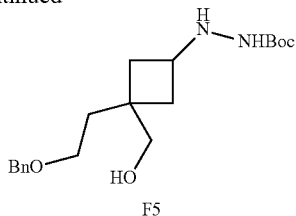

F5

To a 1 L reactor equipped with mechanical stirrer, thermocouple, reflux condenser and argon inlet was added compound F4 (66.0 g, 1.0 equiv.) and THF (6.0 V, 396 mL). The mixture was stirred and cooled to 0-5° C. Sodium bis(2-methoxyethoxy)aluminium hydride (Red-Al or Vitride) (127.3 ml, 132.3 g, 2.4 equiv.) was added slowly over about 20 minutes, keeping batch temperature <30° C. Note: Gas evolution was observed. When ca. 1/3 to ½ of Red-Al had been added, the mixture turned quite viscous while the gas evolution continued with each drop of Red-Al. The mixture got fairly thick. During the remaining addition the mixture gradually became less viscous as the gas evolution diminished and the color turned towards yellow. At the end, a yellow thinner, readily stirrable solution had formed. The whole addition took ca 15-20 minutes. The mixture was stirred under argon at 20-25° C. for at least 2-3 h and checked by HPLC. The batch was quenched into a 10 wt % aqueous solution of Rochelle salt (7.0 V, 560 mL), keeping batch temperature <30° C. The cloudy mixture was stirred about 15 minutes and then allowed to separate for 15 minutes. The lower aqueous layer was drained and the organic layer concentrated at 40-45° C. batch temperature and vacuum to remove THF. Isopropyl acetate (6.0 V, 480 mL) and 10 wt % aqueous solution of Rochelle salt (7.0 V, 560 mL) were added and the mixture was stirred for about 15 minutes at 45-50° C. and then allowed to separate for 15 minutes. The lower aqueous layer was drained. Water (7.0 V, 560 mL) was added and the mixture was stirred 15-30 minutes at 45-50° C. and then allowed to separate for 15 minutes. The lower aqueous layer was drained and isopropyl acetate was distilled at 40-45° C. batch temperature and vacuum until about 3 V remains. Heptane (6.0 V, 480 mL) was added and the mixture was warmed to 70-75° C. batch temperature to achieve complete dissolution. The solution was cooled slowly to about 60° C. batch temperature and seeded. Slow cooling to 20-25° C. over at least 6 hours gave a white slurry that was filtered on a medium Buchner frit. The cake was rinsed with n-heptane (160.00 ml; 1092.11 mmol; 2.00 V) and dried on the frit with house-vac for 1-2 hours and in a vacuum oven at 35-40° C. for a minimum of 6 h to afford 50 g (74%) of compound F5 as a white solid.

tert-butyl 2-(3-(2-(benzyloxy)ethyl)-3-(hydroxymethyl)cyclobutyl)hydrazine-1-carboxylate

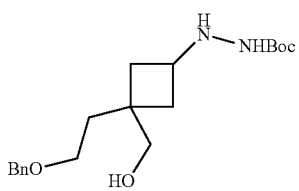 [SMILES: CC(C)(C)OC(=O)NNC1CC(CO)(CCOCc2ccccc2)C1]

$^1$H-NMR (CDCl$_3$); δ7.25-7.39 (m, 5H), 6.03 (br s, 1H), 4.50 (s, 2H), 3.99 (br s, 1H), 3.45-3.58 (m, 5H), 3.30 (br t, J=6 Hz, 1H), 2.04-2.13 (m, 2H), 1.84 (t, J=6 Hz, 2H), 1.52-1.60 (m, 2H), 1.45 (s, 9H). $^{13}$C-NMR (CDCl$_3$); 157.2, 137.7, 128.7, 128.1, 128.0, 80.7, 73.5, 69.2, 67.0, 51.0, 40.3, 36.8, 35.5, 28.5.

1.5. General Procedure for the Synthesis of Compounds of Formula F6

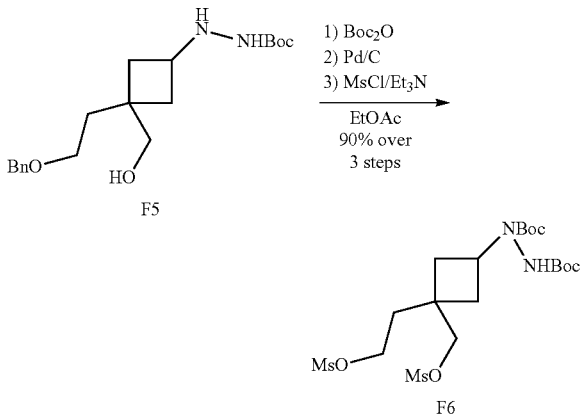

To a reactor equipped with mechanical stirrer, thermocouple, reflux condenser and argon inlet was added compound F5 (50.0 g, 142.67 mmol, 1.0 equiv), Boc$_2$O (32.1 g, 145.53 mmol, 1.02 equiv) and EtOAc (200 mL, 4 vol). The mixture was stirred and heated to 40-45° C. and stirred for 5 hours after which LC analysis indicated complete reaction. The reaction was cooled to 20-25° C. To a pressure reactor was added palladium on carbon (3.0 g, 1.43 mmol) followed by the ethyl acetate solution of the boc-protected hydrazine derivative. The temperature was set to 25° C. the reactor purged with nitrogen and hydrogen. The reactor was pressurized with 50 psi of hydrogen and the contents stirred at 25° C. for 5 hours (the hydrogen uptake lasted for about 90 minutes). A sample was analyzed by UPLCMS analysis to confirm complete conversion. The ethyl acetate solution was filtered through Celite and the cake washed with additional ethyl acetate (approx. 2×50 mL, 2×1 vol). Distill ethyl acetate under vacuum (~120 mbar) at 45° C. Charge EtOAc (400 mL, 8 vol) and take sample for GC and KF analysis for t-butanol and water content, respectively (Note: Repeat distillation if t-BuOH content by GC is over 0.2% or KF is over 0.1%. In this case, t-BuOH content was 0.77%; repeating distillation afforded 431 g of a solution containing 0.14% t-BuOH and KF 0.01%). To a reactor equipped with mechanical stirrer, thermocouple, reflux condenser and argon inlet was added the ethyl acetate solution of the diol after distillation. To the reactor was added MsCl (23.40 mL, 301.39 mmol, 2.2 equiv) in one portion. The solution was stirred for 5 min and cooled to T$_{batch}$~15° C. at T$_{jacket}$=0-5° C. Triethylamine (48 mL, 342.49 mmol, 2.5 equiv) was added dropwise via addition funnel ~15-20 minutes, maintaining batch temperature <25° C., forming a white suspension (Note: The addition is exothermic. In this case, internal temperature increased to ~25° C. with T$_{jacket}$=5° C. An impurity has been observed to form at longer addition times). The temperature was adjusted to T$_{jacket}$=20° C. and the suspension stirred about 15 minutes and analyzed by UPLCMS. The reaction was quenched by addition of 3% aqueous sodium bicarbonate solution (250 ml, 5 vol). The mixture was stirred for about 15 minutes at 20-25° C. and then allowed to separate for about 15 minutes. The lower aqueous layer was drained (Note: The recommended pH of the aqueous layer is 8-9). Water (250 mL, 5 vol) was added. The mixture was stirred for about 15 minutes at 20-25° C. and then allowed to separate for about 15 minutes. The lower aqueous layer was drained (Note: The recommended pH of the aqueous layer is 7-8). Ethyl acetate was distilled at 40-45° C. batch temperature and vacuum until about (~250 mL, 5 vol) remained. Heptane (~250 mL, 5 vol) was added slowly, maintaining batch temperature at 40-45° C. The distillation was continued at 40-45° C. until (~250 mL, 5 vol) remained. Additional n-heptane (100 mL, 2 vol) was added slowly maintaining temperature at 40-45° C. The slurry was cooled to 20-25° C. and stirred for at least 1 hour and filtered. The cake was washed with n-heptane (50 ml, 1 vol) and dried at 35-40° C. using full vacuum with a slow nitrogen bleed overnight to afford compound F6 in 90-95% yield.

di-tert-butyl 1-(3-(2-((methylsulfonyl)oxy)ethyl)-3-(((methylsulfonyl)oxy)methyl)cyclobutyl)hydrazine-1,2-dicarboxylate

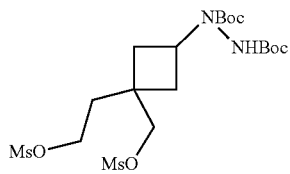

$^1$H-NMR (CDCl$_3$); δ6.05 (br s, 1H), 4.68 (br s, 1H), 4.29 (t, J=6.4 Hz, 2H), 4.24 (br s, 2H), 3.05 (s, 3H), 3.01 (s, 3H), 2.23 (br t, J=10 Hz, 2H), 2.12 (br t, J=10 Hz, 2H), 2.04 (t, J=6.4 Hz, 2H), 1.49 (s, 9H), 1.45 (s, 9H). $^{13}$C-NMR (CDCl$_3$); 156.3, 154.7, 81.7, 73.1, 66.3, 47.4, 46.2, 37.6, 37.5, 36.8, 34.6, 34.1, 28.4, 28.3.

1.6. General Procedure for the Synthesis of Compounds of Formula II

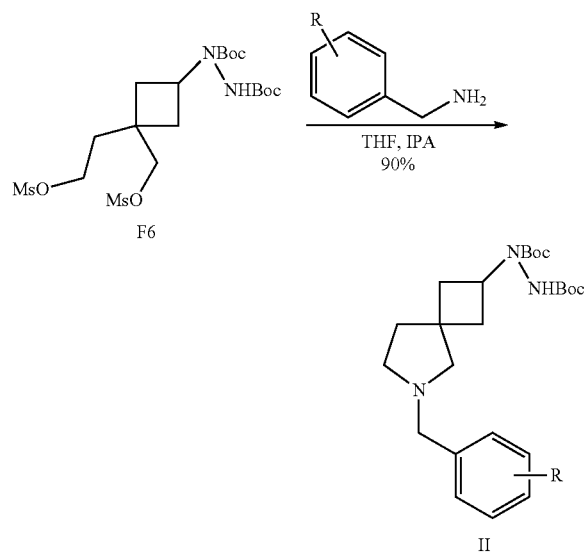

To a reactor under inert atmosphere equipped with mechanical stirrer, thermocouple, reflux condenser and argon inlet was added benzylamine (125 mL, 1145.4 mmol, 5 equiv). The solution was stirred and heated to 90-95° C. with T$_{jacket}$=100° C. A solution of compound F6 (120 g, 229.08 mmol, 1.0 equiv) in THF (360 mL, 3 vol) was added in 3 equal portions, distilling the THF from each portion so the temperature reached 90-95° C. before addition of the next portion (Note: The addition should be done in NLT 1 h. The internal batch temperature after the third addition may be 100-105° C.). The mixture was stirred at 90-95° C. for at least 30 minutes and then analyzed by HPLC. Isopropanol (240 mL, 2 vol) was added over about 10 minutes (Note: the charge rate was adjusted to control the batch temperature to 70-75° C. during the addition). Water (240 mL, 2 vol) was then added over about 10 min (Note: the charge rate was adjusted to control the batch temperature to 70-75° C. during the addition). The batch was cooled to 60-65° C. and seeds of compound II (5 g in 20 mL water) were added. The batch was cooled to 50-55° C. (Note: the batch will thicken. Adjust agitation rate accordingly as needed to maintain adequate stirring. Add water from next operation if stirring becomes difficult). Water (480 mL, 4 vol) was added slowly over about 30 min keeping temperature at 50-55° C. The batch was cooled to 20-25° C. over about 3 hours and stirred for about 2 hours and filtered. The reactor and filter cake was rinsed with 10% isopropanol/water (120 mL) followed by water (120 mL). The solids were dried at 50-55° C. using full vacuum with a slow nitrogen bleed for at least 12 hours to afford compound II as an off-white solid in about 90% yield.

di-tert-butyl 1-(6-benzyl-6-azaspiro[3.4]octan-2-yl)hydrazine-1,2-dicarboxylate

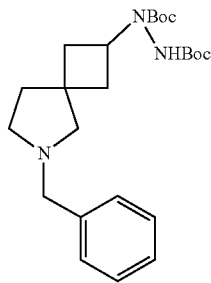 [SMILES: CC(C)(C)OC(=O)NN(C(=O)OC(C)(C)C)C1CC2(CCN(Cc3ccccc3)C2)C1]

$^1$H-NMR (CDCl$_3$); δ7.23-7.32 (m, 5H), 6.10 (br s, 1H), 4.52 (br s, 1H), 3.60 (s, 2H), 2.55 (br s, 4H), 2.18 (br s, 2H), 2.07 (br s, 2H), 1.84 (t, J=7.5 Hz, 2H), 1.47 (s, 9H), 1.44 (s, 9H). $^{13}$C-NMR (CDCl$_3$); 156.0, 154.9, 139.3, 128.9, 128.4, 127.0, 81.2, 81.1, 66.3, 60.7, 53.8, 47.8, 47.4, 40.3, 39.2, 38.0, 28.4, 28.3.

What is claimed is:
1. A compound of formula (II):

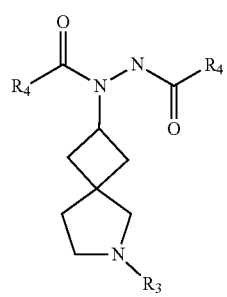

wherein R₃ is chosen from hydrogen, halogen, halo-$C_{1-4}$-alkyl, $C_{1-4}$-alkyl, $C_{1-4}$-alkoxy, —CN, halo-$C_{1-4}$-alkoxy, acyl, acyloxy, alkylaryl or cycloalkyl; and R₄ is hydrogen, halogen, halo-$C_{1-4}$-alkyl, $C_{1-4}$-alkyl, $C_{1-4}$-alkoxy, aryloxy, cycloalkyl or alkylaryl; or an acceptable salt or hydrate thereof.

2. A method of making a compound of formula (II):

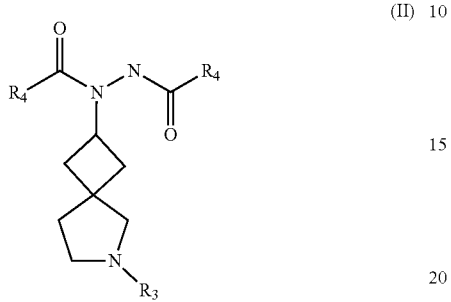
(II)

comprising the steps of:
(i) converting a compound of formula F to a compound of formula F1

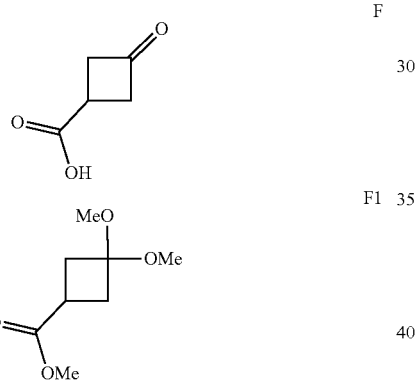

F

F1

(ii) coupling a compound of formula F1 with a compound F2

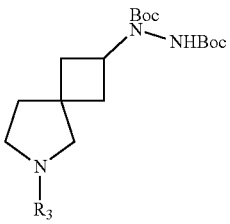
F2 to derive a compound of formula F7,

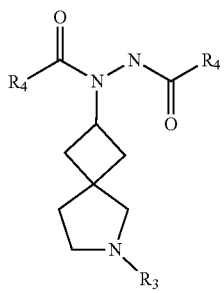
F7

(iii) converting the compound of formula F7 to a compound of Formula (II)

(II)

wherein R₃ is chosen from hydrogen, halogen, halo-$C_{1-4}$-alkyl, $C_{1-4}$-alkyl, $C_{1-4}$-alkoxy, —CN, halo-$C_{1-4}$-alkoxy, acyl, acyloxy, alkylaryl or cycloalkyl; and R₄ is hydrogen, halogen, halo-$C_{1-4}$-alkyl, $C_{1-4}$-alkyl, $C_{1-4}$-alkoxy, aryloxy, cycloalkyl or alkylaryl; or an acceptable salt or hydrate thereof.

* * * * *